United States Patent
Ganz et al.

(10) Patent No.: US 10,835,504 B2
(45) Date of Patent: Nov. 17, 2020

(54) COMPOSITIONS TO TREAT ANAL ITCH

(71) Applicant: G&S Laboratories, Inc., Eagan, MN (US)

(72) Inventors: Robert A. Ganz, Eagan, MN (US); Mo E. Saremi, Eagan, MN (US); William Christopfel, Edina, MN (US)

(73) Assignee: G&S Laboratories, Inc., Eagan, MN (US)

( * ) Notice: Subject to any disclaimer, the term of this patent is extended or adjusted under 35 U.S.C. 154(b) by 0 days.

(21) Appl. No.: 16/388,649

(22) Filed: Apr. 18, 2019

(65) Prior Publication Data

US 2019/0321312 A1 Oct. 24, 2019

Related U.S. Application Data

(60) Provisional application No. 62/659,527, filed on Apr. 18, 2018.

(51) Int. Cl.
| | | |
|---|---|---|
| *A61K 31/16* | (2006.01) | |
| *A61K 31/44* | (2006.01) | |
| *A61K 9/00* | (2006.01) | |
| *A61K 33/40* | (2006.01) | |
| *A61K 31/167* | (2006.01) | |
| *A61K 31/4406* | (2006.01) | |
| *A61K 47/02* | (2006.01) | |
| *A61P 17/04* | (2006.01) | |
| *A61K 47/46* | (2006.01) | |
| *A61K 47/44* | (2017.01) | |

(52) U.S. Cl.
CPC .......... *A61K 31/167* (2013.01); *A61K 9/0031* (2013.01); *A61K 31/4406* (2013.01); *A61K 47/02* (2013.01); *A61K 47/44* (2013.01); *A61K 47/46* (2013.01); *A61P 17/04* (2018.01)

(58) Field of Classification Search
CPC ................ A61K 9/0014; A61K 31/167; A61K 31/4406; A61K 47/44; A61K 9/06
USPC .......................... 424/400, 614; 514/626, 355
See application file for complete search history.

(56) References Cited

U.S. PATENT DOCUMENTS

| | | |
|---|---|---|
| 9,345,747 B2 | 5/2016 | Bastia et al. |
| 9,725,483 B2 | 8/2017 | Garcia Anton |
| 10,117,826 B2 | 11/2018 | Pham |
| 2003/0082219 A1* | 5/2003 | Warren ............. A61F 13/51305 424/401 |
| 2013/0245575 A1* | 9/2013 | Griffin .................... A61K 36/53 604/290 |
| 2014/0303094 A1 | 10/2014 | Bastia et al. |
| 2015/0140046 A1 | 5/2015 | Ferrer Montiel |
| 2017/0128392 A1* | 5/2017 | Maurello ............. A61K 31/355 |
| 2019/0105261 A1 | 4/2019 | Waugh |
| 2019/0247299 A1 | 8/2019 | Cameron |
| 2019/0298699 A1 | 10/2019 | Waugh |
| 2019/0321427 A1 | 10/2019 | Ganz et al. |

OTHER PUBLICATIONS

Digennaro et al., "Prospective multicenter observational trial on the safety and efficacy of LEVORAG Emulgel in the treatment of acute and chronic anal fissure," Tech Coloproctal, 2015, 19:287-292.

Marellucci et al., "Myoxinol ointment for the treatment of acute fissure," Updates Surg., 2017, 69:499-503.

Poh et al., "Innovations in chronic anal fissure treatment: A systematic review," World J. Gastrointest Surg., 2010, 2(7):231-241.

Renzi et al., "Myoxinol (Hydrolyzed Hibiscus esculentus Extract) in the Cure of Chronic Anal Fissure: Early Clinical and Functional Outcomes," Gastroenterology Research and Practice, 2015, vol. 2015, Article ID 567920, 4 pages.

Ansair et al., "Pruritus Ani", Clin Colon Rectal Surg., 2016, 29:38-42.

* cited by examiner

*Primary Examiner* — Shengjun Wang
(74) *Attorney, Agent, or Firm* — Fish & Richardson P.C.

(57) ABSTRACT

The present disclosure relates to topical compositions comprising one or more topical anesthetics or analgesics; a vitamin B3 compound; and a coating agent. In some embodiments, the composition comprises about 1% to about 10% w/w of the composition of the topical anesthetic, topical analgesic, or a combination thereof; about 1% to about 10% w/w of the composition of the vitamin B3 compound; and about 5% to about 50% w/w of the composition of the coating agent. In some embodiments, the composition further includes a pharmaceutically acceptable base. In some embodiments, the pharmaceutically acceptable base comprises about 35% to about 85% w/w of the composition of a pharmaceutically acceptable oil; about 1% to about 20% w/w of the composition of a pharmaceutically acceptable wax; or a combination thereof. Such compositions are useful for treating anal itch or pruritus ani.

18 Claims, No Drawings

COMPOSITIONS TO TREAT ANAL ITCH

CROSS-REFERENCE TO RELATED APPLICATIONS

This application claims the benefit of U.S. provisional Application No. 62/659,527 filed on Apr. 18, 2018, the contents of which is hereby incorporated by reference in its entirety.

TECHNICAL FIELD

The present disclosure relates to topical compositions comprising one or more of a topical anesthetic, topical analgesic, or a combination thereof; a vitamin B3 compound; and a coating agent. Such compositions are useful for treating pruritus ani and reducing anal itch.

BACKGROUND

Pruritus ani or anal itch is the unpleasant sensation of the skin or tissue around the anus producing a desire to scratch. Pruritus ani or itching of the anal region can be caused by, for example, diarrhea or frequent loose stools, multiple loose or soft stools, stool that adheres to the anus and is not entirely cleared post defecation, leakage of stool from rectal incontinence or frequent passage of gas with some stool leakage, parasites that affect the gastrointestinal tract, excess anal moisture or perspiration, or yeast or candida overgrowth affecting the anal region. Subsequent scratching may cause injury to the skin or tissue producing a larger area of irritated skin, which makes the problem worse. Current treatments focus on restoring the skin in the perianal region to clean, dry, intact, and asymptomatic skin.

SUMMARY

Provided herein are topical compositions comprising one or more of a topical anesthetic, topical analgesic, or a combination thereof; a vitamin B3 compound; and a coating agent. Also, provided herein are topical compositions comprising a topical anesthetic, topical analgesic, or a combination thereof; a coating agent; and a vitamin B3 compound. In some embodiments, a composition as described herein further comprises a pharmaceutically acceptable base. In some embodiments, the pharmaceutically acceptable base comprises a pharmaceutically acceptable oil, a pharmaceutically acceptable wax or a combination thereof.

In some embodiments, the composition comprises about 1% to about 10% w/w of the composition of the topical anesthetic, topical analgesic, or a combination thereof.

In some embodiments, the composition comprises about 5% to about 50% w/w of the composition of the coating agent.

In some embodiments, the composition comprises about 1% to about 10% w/w of the composition of the vitamin B3 compound.

In some embodiments, the composition further comprises a pharmaceutically acceptable base, wherein the pharmaceutically acceptable base comprises a pharmaceutically acceptable oil, and the composition comprises about 35% to about 85% w/w of the composition of the pharmaceutically acceptable oil. In some embodiments, the composition further comprises a pharmaceutically acceptable base, wherein the pharmaceutically acceptable base comprises a pharmaceutically acceptable wax and the composition comprises about 1% to about 20% w/w of the composition of the pharmaceutically acceptable wax.

In some embodiments, the composition comprises:
about 1% to about 10% w/w of the composition of the topical anesthetic, topical analgesic, or a combination thereof;
about 5% to about 50% w/w of the composition of the coating agent; and
about 1% to about 10% w/w of the composition of the vitamin B3 compound.

In some embodiments, the composition further comprises a pharmaceutically acceptable base, wherein the pharmaceutically acceptable base comprises a pharmaceutically acceptable wax, oil, or a combination thereof and the composition comprises:
about 35% to about 85% w/w of the composition of the pharmaceutically acceptable oil;
about 1% to about 20% w/w of the composition of the pharmaceutically acceptable wax; or
a combination thereof.

In some embodiments, the composition comprises:
about 5% w/w of the composition of the topical anesthetic, topical analgesic, or a combination thereof;
about 25% w/w of the composition of the coating agent; and
about 5% w/w of the composition of the vitamin B3 compound.

In some embodiments, the composition further comprises a pharmaceutically acceptable base, wherein the pharmaceutically acceptable base comprises a pharmaceutically acceptable wax, oil, or a combination thereof and the composition comprises:
about 55% w/w of the composition of the pharmaceutically acceptable oil;
about 10% w/w of the composition of the pharmaceutically acceptable wax; or a combination thereof.

In some embodiments, the composition comprises a topical anesthetic, and the topical anesthetic is an amino ester local anesthetic. In some embodiments, the amino ester local anesthetic is selected from the group consisting of: benzocaine, chloroprocaine, cocaine, proparacaine, tetracaine, procaine, cinchocaine (dibucaine), cyclomethycaine, and a combination thereof.

In some embodiments, the composition comprises a topical anesthetic, and the topical anesthetic is an amino amide local anesthetic. In some embodiments, the amino amide local anesthetic is selected from the group consisting of: articaine, bupivacaine, dibucaine, lidocaine, mepivacaine, prilocaine, ropivacaine, levobupivacaine, and a combination thereof. In some embodiments, the amino amide local anesthetic comprises lidocaine. In some embodiments, the topical anesthetic comprises lidocaine. In some embodiments, the topical anesthetic is lidocaine.

In some embodiments, the composition comprises a topical analgesic. In some embodiments, the topical analgesic is selected from the group consisting of: capsaicin, acetylsalicylic acid, ketoprofen, piroxicam, diclofenac, indomethacin, ketorolac, rofecoxib, celecoxib, methyl salicylate, monoglycol salicylate, aspirin, indomethacin, ibuprofen, naproxen, pranoproten, tenoproten, sulindac, tenclotenac, clidanac, flurbiprofen, fentiazac, bufexamac, piroxicam, pentazocine, diclofenac-misoprostol, diclofenac epolamine, diclofenac sodium, menthol, camphor, trolamine salicylate, nitroglycerin, ketamine, clonidine hydrochloride, cannabinoids, and a combination thereof.

In some embodiments, the vitamin B3 compound is selected from the group consisting of: niacin, niacinamide, amino acid derivatives of nicotinic acid, nucleoside derivatives of nicotinic acid, nicotinyl alcohol esters of carboxylic acids, nicotinic acid N-oxide, niacinamide N-oxide, nicotinic acid esters, and a combination thereof. In some embodiments, the vitamin B3 compound comprises niacinamide. In some embodiments, the vitamin B3 compound is niacinamide.

In some embodiments, the coating agent comprises zinc oxide, calamine, witch hazel, ephedrine, bismuth oxide, or a combination thereof. In some embodiments, the coating agent comprises zinc oxide.

In some embodiments, the composition comprises a pharmaceutically acceptable base, wherein the pharmaceutically acceptable base comprises a pharmaceutically acceptable oil comprising triglycerides.

In some embodiments, the composition comprises a pharmaceutically acceptable base, wherein the pharmaceutically acceptable base comprises a pharmaceutically acceptable oil comprising a plant oil. In some embodiments, the composition comprises a pharmaceutically acceptable base, wherein the pharmaceutically acceptable base comprises a plant oil selected from the group consisting of: avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, of on oil, andiroba oil, and tucuma oil, and a combination thereof.

In some embodiments, the composition comprises a pharmaceutically acceptable base, wherein the pharmaceutically acceptable base comprises a pharmaceutically acceptable oil comprising a synthetic oil. In some embodiments, the composition comprises a pharmaceutically acceptable base, wherein the pharmaceutically acceptable base comprises a pharmaceutically acceptable synthetic oil selected from the group consisting of: capric/caprylic triglycerides, isopropyl palmitate, etherified oils, dicaprylether, octyldodecanol, silicone oils, dimethicone oil, cyclomethicone, propoxylated fatty alcohols, triolein, tristearin glyceryl dilaurate, and a combination thereof.

In some embodiments, the composition comprises a pharmaceutically acceptable base, wherein the pharmaceutically acceptable base comprises a pharmaceutically acceptable oil comprising an animal oil. In some embodiments, the composition comprises a pharmaceutically acceptable base, wherein the pharmaceutically acceptable base comprises a pharmaceutically acceptable animal oil selected from the group consisting of: mink oil, egg yolk oil, fish oil, turtle oil, lanolin, cod liver oil, crocodile oil, emu oil, horse oil, squalene oil, shark liver oil, and a combination thereof.

In some embodiments, the composition comprises a pharmaceutically acceptable base, wherein the pharmaceutically acceptable base comprises a pharmaceutically acceptable oil selected from the group consisting of: palmitic acid, oleic acid, ng acid, linoleic acid, stearic acid, α-linolenic acid, and a combination thereof.

In some embodiments, the composition comprises a pharmaceutically acceptable base, wherein the pharmaceutically acceptable base comprises a pharmaceutically acceptable wax selected from the group consisting of: beeswax, candelilla wax, cotton wax, carnauba wax, bayberry wax, insect wax (wax secreted by Ericerus pela), spermaceti, montan wax, bran wax, lanolin, capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, POE hydrogenated lanolin alcohol ethers, and a combination thereof. In some embodiments, the composition comprises a pharmaceutically acceptable base, wherein the pharmaceutically acceptable base comprises a pharmaceutically acceptable wax comprising beeswax.

In some embodiments, the composition comprises a pharmaceutically acceptable base, wherein the pharmaceutically acceptable base comprises a pharmaceutically acceptable oil, and the composition comprises about 55% w/w of the composition of the pharmaceutically acceptable oil. In some embodiments, the composition comprises a pharmaceutically acceptable base, wherein the pharmaceutically acceptable base comprises a pharmaceutically acceptable oil, and the pharmaceutically acceptable oil comprises sunflower seed oil and olive oil. In some embodiments, the composition comprises a pharmaceutically acceptable base, wherein the pharmaceutically acceptable base comprises a pharmaceutically acceptable oil, and the pharmaceutically acceptable oil comprises sunflower seed oil present in an amount of about 50% w/w of the composition of the composition. In some embodiments, the composition comprises a pharmaceutically acceptable base, wherein the pharmaceutically acceptable base comprises a pharmaceutically acceptable oil, and the pharmaceutically acceptable oil comprises olive oil present in an amount of about 5% w/w of the composition of the composition.

In some embodiments, the composition comprises a topical anesthetic and the topical anesthetic comprises lidocaine present in an amount of about 5% w/w of the composition of the composition. In some embodiments, the composition comprises a topical anesthetic, and the topical anesthetic is lidocaine present in an amount of about 5% w/w of the composition.

In some embodiments, the coating agent comprises zinc oxide present in an amount of about 25% w/w of the composition of the composition. In some embodiments, the coating agent is zinc oxide present in an amount of about 25% w/w of the composition of the composition.

In some embodiments, the vitamin B3 compound comprises niacinamide present in an amount of about 5% w/w of the composition of the composition. In some embodiments, the vitamin B3 compound is niacinamide present in an amount of about 5% w/w of the composition of the composition.

In some embodiments, the composition comprises a pharmaceutically acceptable base, wherein the pharmaceutically acceptable base comprises a pharmaceutically acceptable wax and the pharmaceutically acceptable wax comprises beeswax present in an amount of about 10% w/w of the composition of the composition.

In some embodiments, the coating agent is zinc oxide; the vitamin B3 compound is niacinamide; and the pharmaceutically acceptable wax is beeswax.

In some embodiments, the composition comprises:
sunflower seed oil;
olive oil;
lidocaine;
zinc oxide;
niacinamide; and
beeswax.

In some embodiments, the composition comprises:
about 25% to about 75% w/w of the composition sunflower seed oil;
about 1% to about 10% w/w of the composition olive oil;
about 1% to about 10% w/w of the composition lidocaine;
about 5% to about 50% w/w of the composition zinc oxide;
about 1% to about 10% w/w of the composition niacinamide; and
about 1% to about 20% w/w of the composition beeswax.

In some embodiments, the composition comprises:
about 50% w/w of the composition sunflower seed oil;
about 5% w/w of the composition olive oil;
about 5% w/w of the composition lidocaine;
about 25% w/w of the composition zinc oxide;
about 5% w/w of the composition niacinamide; and
about 10% w/w of the composition beeswax.

In some embodiments, the composition further comprises colloidal oatmeal. In some embodiments, the composition further comprises a pharmaceutically acceptable butter and the pharmaceutically acceptable butter is selected from the group consisting of: shea butter, cocoa butter, illipe butter, mango butter, almond butter, kokum butter, sal butter, cupuacu butter, aloe butter, avocado butter, chaulmoogra butter, dhupu butter, hemp butter, kukui nut butter, macadamia nut butter, jojoba butter, tucuma butter, and a combination thereof.

In some embodiments, the composition includes at least one carrier, diluent, excipient, or a combination thereof.

In some embodiments, the composition is in the form of a paste, gel, cream, spray, suppository, mousse, emollient, ointment, foam, or suspension.

Also provided herein are methods of treating pruritus ani in a subject in need thereof, the method comprising administering to the subject a therapeutically effective amount of the composition as provided herein. In some embodiments, the pruritus ani is associated with one or more of the following: diarrhea, rectal incontinence, stool leakage, parasitic infections of the GI tract, excess anal moisture, excess anal perspiration, fungal overgrowth in the anal region, psoriasis, Crohn's disease, hemorrhoids, anal fissures, bacterial skin infections, viral infections (e.g., anal warts), seborrheic dermatitis, atopic dermatitis, contact dermatitis, lichen planus, lichen simplex, lichen sclerosis, diabetes mellitus, leukemia and lymphoma, kidney failure, liver diseases (obstructive jaundice), iron deficiency anemia, and hyperthyroidism. In some embodiments, the subject is an infant, a child, an adolescent, or an elderly subject.

Also provided herein are methods for reducing anal itching in a subject in need thereof the method comprising administering to the subject a therapeutically effective amount of the composition as provided herein. In some embodiments, the anal itching is associated with one or more of the following: diarrhea, rectal incontinence, stool leakage, parasitic infections of the GI tract, excess anal moisture, excess anal perspiration, fungal overgrowth in the anal region, psoriasis, Crohn's disease, hemorrhoids, anal fissures, bacterial skin infections, viral infections (e.g., anal warts), seborrheic dermatitis, atopic dermatitis, contact dermatitis, lichen planus, lichen simplex, lichen sclerosis, diabetes mellitus, leukemia and lymphoma, kidney failure, liver diseases (obstructive jaundice), iron deficiency anemia, and hyperthyroidism. In some embodiments, the subject is an infant, a child, an adolescent, or an elderly subject.

Also provided herein are methods for reducing itching in a subject in need thereof, the method comprising administering to the subject a therapeutically effective amount of the composition as provided herein. In some embodiments, at least a portion of the skin of the subject itches. In some embodiments, the itching on the subject is located on the head, an arm, torso, a leg, neck, a hand, or a foot of the subject. In some embodiments, the subject is an infant, a child, an adolescent, or an elderly subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, databases entries, and other references mentioned herein are incorporated by reference in their entirety. In case of conflict, the present specification, including definitions, will control.

DETAILED DESCRIPTION

Pruritus ani or anal itch is probably the most common ano-rectal disorder in the developed world. Pruritus ani or itching of the anal region can have multiple causes including diarrhea or frequent loose stools, multiple loose or soft stools, stool that adheres to the anus and is not entirely cleared post defecation, leakage of stool from rectal incontinence or frequent passage of gas with some stool leakage, parasites that affect the gastrointestinal tract, excess anal moisture or perspiration, or yeast or candida overgrowth affecting the anal region. Subsequent scratching may cause injury to the skin or tissue producing a larger area of irritated skin, which can lead to a cycle known as the itch-scratch-itch cycle. Scratching the itch causes the release of inflammatory chemokines, which secondarily worsens the itch by causing redness, increased itching and dry skin, thereby causing a "rebound" effect.

The main goal of current treatments for anal itch is to restore the skin in the perianal region to clean, dry, intact, and asymptomatic skin. For example, repetitively cleaning the region with non-soap warm water and then drying the area. Steroid ointments can also be tried, either with or without antifungal or antibiotic additives.

There is no strict definition of pruritus ani, but in practice the presence the following symptoms or signs has been used: a) persistent itch in the ano-rectal region; and b) consistent physical exam with erythema, inflammation and/or breaks in the anoderm.

Accordingly, the present application provides topical compositions comprising a topical anesthetic, a topical analgesic, or a combination thereof, a vitamin B3 compound, and a coating agent useful in the treatment of pruritus ani or anal itch

Definitions

As used herein, the phrases "anal itch is associated with" or "pruritus ani is associated with" a disease, disorder, or condition encompasses a subject with anal itch or pruritus ani that is diagnosed with, was previously diagnosed with, or has symptoms associated with the disease, disorder, or condition.

As used herein, the term "coating agent" refers to an agent that coats skin or tissue that may have protective and/or antibacterial properties.

As used herein, the phrases an "effective amount" or a "therapeutically effective amount" of an active agent or ingredient, or pharmaceutically active agent or ingredient, refer to an amount of the pharmaceutically active agent sufficient enough to reduce or eliminate one or more symptoms of the disorder or to effect a cure upon administration. Effective amounts of the pharmaceutically active agent will vary with the kind of pharmaceutically active agent chosen, the particular condition or conditions being treated, the severity of the condition, the duration of the treatment, the specific components of the composition being used, and like factors. For example, the presently described compositions can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

As used herein, "subject" or "patient" refers to any subject, particularly a mammalian subject, for whom diagnosis, prognosis, or therapy is desired, for example, a human.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of one or more symptoms associated therewith, or provide improvement to a patient or subject's quality of life.

Reference to the term "about" has its usual meaning in the context of pharmaceutical compositions to allow for reasonable variations in amounts that can achieve the same effect and also refers herein to a value of plus or minus 10% of the provided value. For example, "about 20" means or includes amounts from 18 to and including 22.

Compositions and Pharmaceutical Compositions

Provided herein are topical compositions having one or more of a topical anesthetic, topical analgesic, or a combination thereof; a vitamin B3 compound; and a coating agent. In some embodiments, a topical composition provided herein comprises a topical anesthetic, topical analgesic, or a combination thereof; and a vitamin B3 compound. In some embodiments, a topical composition provided herein comprises a topical anesthetic, topical analgesic, or a combination thereof; and a coating agent. In some embodiments, a topical composition provided herein comprises a vitamin B3 compound and a coating agent. Also, provided herein are topical compositions having a topical anesthetic, topical analgesic, or a combination thereof; a vitamin B3 compound; and a coating agent. In some embodiments, a topical composition as provided herein also comprises a pharmaceutically acceptable base. In some embodiments, the pharmaceutically acceptable base comprises a pharmaceutically acceptable oil, a pharmaceutically acceptable wax, a pharmaceutically acceptable butter, or a combination thereof.

In some embodiments, a topical composition as provided herein comprises a topical anesthetic, topical analgesic, or a combination thereof; a vitamin B3 compound; and a coating agent. In some embodiments, the composition also includes a pharmaceutically acceptable base. In some embodiments, the pharmaceutically acceptable base comprises a pharmaceutically acceptable oil, a pharmaceutically acceptable wax, a pharmaceutically acceptable butter, or a combination thereof.

In some embodiments, a topical composition as provided herein composition comprises about 1% to about 10% w/w of the composition of the topical anesthetic, topical analgesic, or a combination thereof. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition of the topical anesthetic, topical analgesic, or a combination thereof. In some embodiments, the composition comprises about 4% to about 6% w/w of the composition of the topical anesthetic, topical analgesic, or a combination thereof. In some embodiments, the composition comprises about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5% w/w of the composition, or about 7% w/w of the composition of the topical anesthetic, topical analgesic, or a combination thereof.

In some embodiments, the topical anesthetic, topical analgesic, or a combination thereof is present in an amount of about 1% to about 10% w/w of the composition. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition. In some embodiments, the topical anesthetic, topical analgesic, or a combination thereof is present in an amount of about 4% to about 6% w/w of the composition. In some embodiments, the topical anesthetic, topical analgesic, or a combination thereof is present in an amount of about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5 w/w of the composition, or about 7% w/w of the composition.

In some embodiments, the topical anesthetic comprises an amino ester local anesthetic. In some embodiments, the amino ester local anesthetic comprises benzocaine, chloroprocaine, cocaine, proparacaine, tetracaine, procaine, cinchocaine (dibucaine), cyclomethycaine, or a combination thereof.

In some embodiments, the topical anesthetic comprises an amino ester local anesthetic. In some embodiments, the amino ester local anesthetic comprises benzocaine, chloroprocaine, cocaine, proparacaine, tetracaine, procaine, cinchocaine (dibucaine), cyclomethycaine, or a combination thereof.

In some embodiments, the topical anesthetic is an amino ester local anesthetic. In some embodiments, the amino ester local anesthetic is selected from the group consisting of: benzocaine, chloroprocaine, cocaine, proparacaine, tetracaine, procaine, cinchocaine (dibucaine), cyclomethycaine, and a combination thereof. In some embodiments, the topical anesthetic comprises lidocaine.

In some embodiments, the topical anesthetic is an amino ester local anesthetic. In some embodiments, the amino ester local anesthetic is selected from the group consisting of: benzocaine, chloroprocaine, cocaine, proparacaine, tetracaine, procaine, cinchocaine (dibucaine), cyclomethycaine, and a combination thereof. In some embodiments, the topical anesthetic is lidocaine.

In some embodiments, the topical analgesic comprises capsaicin, acetylsalicylic acid, ketoprofen, piroxicam, diclofenac, indomethacin, ketorolac, rofecoxib, celecoxib, methyl salicylate, monoglycol salicylate, aspirin, indomethacin, ibuprofen, naproxen, pranoproten, tenoproten, sulindac, tenclotenac, clidanac, flurbiprofen, fentiazac, bufexamac, piroxicam, pentazocine, diclofenac-misoprostol, diclofenac epolamine, diclofenac sodium, menthol, camphor, trolamine salicylate, nitroglycerin, ketamine, clonidine hydrochloride, and cannabinoids (e.g., delta8-tetrahydrocannabinol [delta8-THC], cannabidiol [CBD], cannabinol [CBN]), extracted from *Cannabis sativa* L, or a combination thereof.

In some embodiments, the topical analgesic is selected from the group consisting of: capsaicin, acetyl salicylic acid, ketoprofen, piroxicam, diclofenac, indomethacin, ketorolac, rofecoxib, celecoxib, methyl salicylate, monoglycol salicylate, aspirin, indomethacin, ibuprofen, naproxen, pranoproten, tenoproten, sulindac, tenclotenac, clidanac, flurbiprofen, fentiazac, bufexamac, piroxicam, pentazocine, diclofenac-misoprostol, diclofenac epolamine, diclofenac sodium, menthol, camphor, trolamine salicylate, nitroglycerin, ketamine, clonidine hydrochloride, and cannabinoids (e.g., delta8-tetrahydrocannabinol [delta8-THC], cannabidiol [CBD], cannabinol [CBN]), extracted from *Cannabis sativa* L, and a combination thereof.

In some embodiments, the topical anesthetic, topical analgesic, or a combination thereof comprises lidocaine. In some embodiments, the composition comprises about 1% to about 10% w/w of the composition of the lidocaine. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition of the lidocaine. In some embodiments, the composition comprises about 4% to about 6% w/w of the composition of the lidocaine. In some embodiments, the composition comprises about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5% w/w of the composition, or about 7% w/w of the composition of the lidocaine.

In some embodiments, the topical anesthetic, topical analgesic, or a combination thereof is lidocaine. In some embodiments, the lidocaine is present in an amount of about 1% to about 10% w/w of the composition. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition. In some embodiments, the lidocaine is present in an amount of about 4% to about 6% w/w of the composition. In some embodiments, the lidocaine is present in an amount of about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5% w/w of the composition, or about 7% w/w of the composition.

In some embodiments, the topical anesthetic, topical analgesic, or a combination thereof is a combination of lidocaine and an analgesic.

"Vitamin B3 compounds" as used herein include those having the formula:

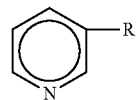

wherein R is —CONH$_2$ (e.g., niacinamide), —C(O)OH (e.g., niacin), or —CH$_2$OH (e.g., nicotinyl alcohol), and include derivatives and salts thereof. Exemplary derivatives of vitamin B3 compounds include, but are not limited to, amino acid derivatives of nicotinic acid, nucleoside derivatives of nicotinic acid (e.g., nicotinamide riboside), nicotinyl alcohol esters of carboxylic acids, nicotinic acid N-oxide, niacinamide N-oxide, and nicotinic acid esters (e.g., $C_1$-$C_{18}$ nicotinic acid esters) including non-vasodilating esters of nicotinic acid.

In some embodiments, a topical composition as provided herein comprises about 1% to about 10% w/w of the composition of the vitamin B3 compound. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition of the vitamin B3 compound. In some embodiments, the composition comprises about 4% to about 6% w/w of the composition of the vitamin B3 compound. In some embodiments, the composition comprises about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5% w/w of the composition, or about 7% w/w of the composition of the vitamin B3 compound.

In some embodiments, the vitamin B3 compound is present in an amount of about 1% to about 10% w/w of the composition. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition. In some embodiments, the vitamin B3 compound is present in an amount of about 4% to about 6% w/w of the composition. In some embodiments, the vitamin B3 compound is present in an amount of about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5% w/w of the composition, or about 7% w/w of the composition.

In some embodiments, the vitamin B3 compound comprises amino acid derivatives of nicotinic acid, nucleoside derivatives of nicotinic acid (e.g., nicotinamide riboside), nicotinyl alcohol esters of carboxylic acids, nicotinic acid N-oxide, niacinamide N-oxide, and nicotinic acid esters (e.g., C1-C18 nicotinic acid esters) including non-vasodilating esters of nicotinic acid, or a combination thereof.

In some embodiments, the vitamin B3 compound is selected from the group consisting of: amino acid derivatives of nicotinic acid, nucleoside derivatives of nicotinic acid (e.g., nicotinamide riboside), nicotinyl alcohol esters of carboxylic acids, nicotinic acid N-oxide, niacinamide N-oxide, and nicotinic acid esters (e.g., C1-C18 nicotinic acid esters) including non-vasodilating esters of nicotinic acid, and a combination thereof. In some embodiments, the vitamin B3 compound is niacinamide.

In some embodiments, the vitamin B3 compound comprises niacinamide, niacin, or a combination thereof. In some embodiments, the vitamin B3 compound comprises niacinamide. In some embodiments, the composition comprises about 1% to about 10% w/w of the composition of the niacinamide. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition of the niacinamide. In some embodiments, the composition comprises about 4% to about 6% w/w of the composition of the niacinamide. In some embodiments, the composition comprises about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5 w/w of the composition, or about 7% w/w of the composition of the niacinamide.

In some embodiments, the vitamin B3 compound is niacinamide, niacin, or a combination thereof. In some embodiments, the vitamin B3 is niacinamide. In some embodiments, the niacinamide is present in an amount of about 1% to about 10% w/w of the composition. For example, about 1% to about 3% w/w of the composition, about 1% to about 4% w/w of the composition, about 1% to about 5% w/w of the composition, about 1% to about 6% w/w of the composition, about 1% to about 7% w/w of the composition, about 1% to about 9% w/w of the composition, about 3% to about 10% w/w of the composition, about 4% to about 10% w/w of the composition, about 5% to about 10% w/w of the composition, about 6% to about 10% w/w of the composition, about 7% to about 10% w/w of the composition, about 3% to about 7% w/w of the composition, about 2% to about 6% w/w of the composition, about 4% to about 7% w/w of the composition, or about 2% to about 8% w/w of the composition. In some embodiments, the niacinamide is present in an amount of about 4% to about 6% w/w of the composition. In some embodiments, the niacinamide is present in an amount of about 3% w/w of the composition, about 3.5% w/w of the composition, about 4% w/w of the composition, about 4.5% w/w of the composition, about 5% w/w of the composition, about 5.5% w/w of the composition, about 6% w/w of the composition, about 6.5 w/w of the composition, or about 7% w/w of the composition.

As used herein, the term "coating agent" refers to an agent that coats skin or tissue that may have protective and/or antibacterial properties. The coating agent can be a gel or cream, but does not have an alcohol base. Exemplary coating agents include, but are not limited to, zinc oxide, calamine (zinc oxide and iron oxide), witch hazel, bismuth oxide, and ephedrine.

In some embodiments, a topical composition as provided herein comprises about 5% to about 50% w/w of the composition of the coating agent. For example, about 5% to about 15% w/w of the composition, about 5% to about 20% w/w of the composition, about 5% to about 25% w/w of the composition, about 5% to about 30% w/w of the composition, about 5% to about 35% w/w of the composition, about 15% to about 50% w/w of the composition, about 20% to about 50% w/w of the composition, about 25% to about 50% w/w of the composition, about 30% to about 50% w/w of the composition about, about 35% to about 50% w/w of the composition, about 10% to about 40% w/w of the composition, about 15% to about 35% w/w of the composition, or about 20% to about 30% w/w of the composition of the coating agent. In some embodiments, the composition comprises about 22 to about 28% w/w of the composition of the coating agent. In some embodiments, the compositions comprises about 10% w/w of the composition, about 15% w/w of the composition, about 20% w/w of the composition, about 25% w/w of the composition, about 30% w/w of the composition, about 35% w/w of the composition or about 40% w/w of the composition of the coating agent.

In some embodiments, the coating agent is present in an amount of about 5% to about 50% w/w of the composition. For example, about 5% to about 15% w/w of the composition, about 5% to about 20% w/w of the composition, about 5% to about 25% w/w of the composition, about 5% to about 30% w/w of the composition, about 5% to about 35% w/w of the composition, about 15% to about 50% w/w of the composition, about 20% to about 50% w/w of the composition, about 25% to about 50% w/w of the composition, about 30% to about 50% w/w of the composition about, about 35% to about 50% w/w of the composition, about 10% to about 40% w/w of the composition, about 15% to about 35% w/w of the composition, or about 20% to about 30% w/w of the composition. In some embodiments, the coating agent is present in an amount of at about 22% to about 28% w/w of the composition. In some embodiments, the coating agent is present in an amount of about 10% w/w of the composition, about 15% w/w of the composition, about 20% w/w of the composition, about 25% w/w of the composition, about 30% w/w of the composition, about 35% w/w of the composition or about 40% w/w of the composition.

In some embodiments, the coating agent comprises zinc oxide, calamine, witch hazel, bismuth oxide, ephedrine, or a combination thereof. In some embodiments, the coating agent comprises zinc oxide.

In some embodiments, the coating agent is selected from the group consisting of: zinc oxide, calamine, witch hazel, bismuth oxide, ephedrine, and a combination thereof. In some embodiments, the coating agent is zinc oxide.

In some embodiments, the coating agent comprises zinc oxide. In some embodiments, the composition comprises about 5% to about 50% w/w of the composition of zinc oxide. For example, about 5% to about 15% w/w of the composition, about 5% to about 20% w/w of the composition, about 5% to about 25% w/w of the composition, about 5% to about 30% w/w of the composition, about 5% to about 35% w/w of the composition, about 15% to about 50% w/w of the composition, about 20% to about 50% w/w of the composition, about 25% to about 50% w/w of the composition, about 30% to about 50% w/w of the composition about, about 35% to about 50% w/w of the composition, about 10% to about 40% w/w of the composition, about 15% to about 35% w/w of the composition, or about 20% to about 30% w/w of the composition of zinc oxide. In some embodiments, the composition comprises about 22 to about 28% w/w of the composition of zinc oxide. In some embodiments, the composition comprises about 10% w/w of the composition, about 15% w/w of the composition, about 20% w/w of the composition, about 25% w/w of the composition, about 30% w/w of the composition, about 35% w/w of the composition or about 40% w/w of the composition of zinc oxide.

In some embodiments, the coating agent is zinc oxide. In some embodiments, the zinc oxide is present in an amount of about 5% to about 50% w/w of the composition. For example, about 5% to about 15% w/w of the composition, about 5% to about 20% w/w of the composition, about 5% to about 25% w/w of the composition, about 5% to about 30% w/w of the composition, about 5% to about 35% w/w of the composition, about 15% to about 50% w/w of the composition, about 20% to about 50% w/w of the composition, about 25% to about 50% w/w of the composition, about 30% to about 50% w/w of the composition about, about 35% to about 50% w/w of the composition, about 10% to about 40% w/w of the composition, about 15% to about 35% w/w of the composition, or about 20% to about 30% w/w of the composition. In some embodiments, the zinc oxide is present in an amount of about 22 to about 28% w/w of the composition. In some embodiments, the zinc oxide is present in an amount of about 10% w/w of the composition, about 15% w/w of the composition, about 20% w/w of the composition, about 25% w/w of the composition, about 30% w/w of the composition, about 35% w/w of the composition or about 40% w/w of the composition.

As used herein, the term "pharmaceutically acceptable base" refers to compounds that are stable, non-irritating, and non-sensitizing and which are useful in preparing topical solid or semi-solid formulations. A pharmaceutically acceptable base can be inert or it can possess dermatological benefits of its own. Exemplary pharmaceutically acceptable bases include, but are not limited to, pharmaceutically acceptable oils such as plant, animal, and synthetic oils, pharmaceutically acceptable waxes, and pharmaceutically acceptable butters.

In some embodiments, a topical composition as provided herein comprises a pharmaceutically acceptable base. In some embodiments, the pharmaceutically acceptable base comprises a pharmaceutically acceptable oil, a pharmaceutically acceptable wax, a pharmaceutically acceptable butter, or a combination thereof. In some embodiments, the pharmaceutically acceptable base comprises a pharmaceutically acceptable oil, a pharmaceutically acceptable wax, or a combination thereof.

In some embodiments, a topical composition as provided herein includes a pharmaceutically acceptable base. In some embodiments, the pharmaceutically acceptable base is a pharmaceutically acceptable oil, a pharmaceutically acceptable wax, a pharmaceutically acceptable butter, or a combination thereof. In some embodiments, the pharmaceutically acceptable base is a pharmaceutically acceptable oil, a pharmaceutically acceptable wax, or a combination thereof.

In some embodiments, a topical composition as provided herein comprises about 35% to about 85% w/w of the composition of the pharmaceutically acceptable oil. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition of the pharmaceutically acceptable oil. In some embodiments, the composition comprises about 50% to about 60% w/w of the composition, about 45% to about 55% w/w of the composition, or about 55% to about 65% w/w of the composition of the pharmaceutically acceptable oil. In some embodiments, the composition comprises about 40% w/w of the composition, about 45% w/w of the composition, about 50% w/w of the composition, about 55% w/w of the composition, about 60% w/w of the composition, about 65% w/w of the composition, or about 70% w/w of the composition of the pharmaceutically acceptable oil.

In some embodiments, the pharmaceutically acceptable oil is present in an amount of about 35% to about 85% w/w of the composition. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition. In some embodiments, the pharmaceutically acceptable oil is present in an amount of about 50% to about 60% w/w of the composition, about 45% to about 55% w/w of the composition, or about 55% to about 65% w/w of the composition. In some embodiments, the pharmaceutically acceptable oil is present in an amount of about 40% w/w of the composition, about 45% w/w of the composition, about 50% w/w of the composition, about 55% w/w of the composition, about 60% w/w of the composition, about 65% w/w of the composition, or about 70% w/w of the composition.

In some embodiments, the compositions described herein can include any one or a combination of pharmaceutically acceptable plant oils. Many plant oils are named by the plant from which the oil is found. For example, rose oil or peppermint oil are derived from rose or peppermint plants, respectively. In some embodiments, the plant oils include oils derived from herbs, flowers, trees, and other plants. Plant oils can be extracted by several method known to those of skill in the art (e.g., steam distilled, enfleurage (i.e., extraction by using fat), maceration, solvent extraction, or mechanical pressing). Plant oils are insoluble in water and are soluble in alcohol, ether, fixed oils (vegetal), and other organic solvents. Typical physical characteristics found in plant oils include boiling points that vary from about 160° to 240° C. and densities ranging from about 0.759 to about 1.096.

Exemplary plant oils include, but are not limited to avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, ojon oil, andiroba oil, and tucuma oil. Other plant oils known to those of skill in the art are also contemplated as being useful when formulated in the compositions described herein.

In some embodiments, the pharmaceutically acceptable oil comprises a plant oil. In some embodiments, the plant oil comprises: avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, ojon oil, andiroba oil, tucuma oil, or a combination thereof.

In some embodiments, the pharmaceutically acceptable oil is a plant oil. In some embodiments, the plant oil is selected from the group consisting of: avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, ojon oil, andiroba oil, tucuma oil, and a combination thereof.

In some embodiments, the pharmaceutically acceptable oil comprises triglycerides. In some embodiments, the triglycerides are of animal or vegetable origin or a combination thereof. In some embodiments, the triglycerides are natural, synthetic, or a combination thereof. In some embodiments, the triglycerides are medium chain triglycerides, mono-, di- and/or triglycerides, or mixtures thereof. Exemplary oils comprising triglycerides include, but are not limited to, sunflower seed oil, olive oil, castor oil, citrate triisocetyl triglycerides having 10-18 carbon atoms, caprylic/capric triglycerides (e.g., Myritol® 318), and egg yolk oil.

The compositions described herein can include any one or a combination of pharmaceutically acceptable animal oils. Animal oils include oils derived from animal substances such as bone, liver, and fat. Exemplary animal oils include, but are not limited to, mink oil, egg yolk oil, fish oil, turtle oil, lanolin, cod liver oil, crocodile oil, emu oil, horse oil, squalene oil, and shark liver oil. Other pharmaceutically acceptable animal oils known to those of skill in the art are also contemplated as being useful when formulated in the compositions described herein.

In some embodiments, the pharmaceutically acceptable oil comprises an animal oil. In some embodiments, the animal oil is selected from the group consisting of: mink oil, egg yolk oil, fish oil, turtle oil, lanolin, cod liver oil, crocodile oil, emu oil, horse oil, squalene oil, shark liver oil, tallow, or a combination thereof.

In some embodiments, the pharmaceutically acceptable oil is an animal oil. In some embodiments, the animal oil is selected from the group consisting of: mink oil, egg yolk oil, fish oil, turtle oil, lanolin, cod liver oil, crocodile oil, emu oil, horse oil, squalene oil, shark liver oil, tallow, and a combination thereof.

The compositions described herein can include any one or a combination of pharmaceutically acceptable synthetic oils. Synthetic oils are oils that are artificially made. Exemplary synthetic oils include, but are not limited to, capric/caprylic triglycerides (e.g., Myritol® 318), isopropyl palmitate, etherified oils (e.g., dicaprylether, octyldodecanol), silicone oils (e.g., dimethicone oil, cyclomethicone), propoxylated fatty alcohols, triolein, and tristearin glyceryl dilaurate. Other pharmaceutically acceptable synthetic oils known to those of skill in the art are also contemplated as being useful when formulated in the compositions described herein.

In some embodiments, the pharmaceutically acceptable oil comprises a synthetic oil. In some embodiments, the synthetic oil comprises isopropyl palmitate, etherified oils (e.g., dicaprylether, octyldodecanol), silicone oils (e.g., dimethicone oil, cyclomethicone), propoxylated fatty alcohols, capric/caprylic triglycerides (e.g., Myritol® 318), triolein, and tristearin glyceryl dilaurate, or a combination thereof.

In some embodiments, the pharmaceutically acceptable oil is a synthetic oil. In some embodiments, the synthetic oil is selected from the group consisting of: isopropyl palmitate, etherified oils (e.g., dicaprylether, octyldodecanol), silicone oils (e.g., dimethicone oil, cyclomethicone), propoxylated fatty alcohols, capric/caprylic triglycerides (e.g., Myritol® 318), triolein, and tristearin glyceryl dilaurate, and a combination thereof.

In some embodiments, the pharmaceutically acceptable oil comprises sunflower seed oil and olive oil. In some embodiments, the composition comprises about 35% to about 85% w/w of the composition of the sunflower seed oil and olive oil. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition of the sunflower seed oil and olive oil. In some embodiments, the composition comprises about 50% to about 60% w/w of the composition, about 45% to about 55% w/w of the composition, or about 55% to about 65% w/w of the composition of the sunflower seed oil and olive oil. In some embodiments, the composition comprises about 40% w/w of the composition, about 45% w/w of the composition, about 50% w/w of the composition, about 55% w/w of the composition, about 60% w/w of the composition, about 65% w/w of the composition, or about 70% w/w of the composition of the sunflower seed oil and olive oil. In some embodiments, the composition comprises about 40% to about 60% w/w of the composition of the sunflower seed oil and about 1% to about 10% w/w of the composition of the olive oil. In some embodiments, the composition comprises about 65% w/w of the composition of the sunflower seed oil and about 5% w/w of the composition of the olive oil.

In some embodiments, the pharmaceutically acceptable oil is sunflower seed oil and olive oil. In some embodiments, the sunflower seed oil and olive oil are present in an amount of about 35% to about 85% w/w of the composition. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition. In some embodiments, the sunflower seed oil and olive oil are present in an amount of about 50% to about 60% w/w of the composition, about 45% to about 55% w/w of the composition, or about 55% to about 65% w/w of the composition. In some embodiments, the sunflower seed oil and olive oil are present in an amount of about 40% w/w of the composition, about 45% w/w of the composition, about 50% w/w of the composition, about 55% w/w of the composition, about 60% w/w of the composition, about 65% w/w of the composition, or about 70% w/w of the composition. In some embodiments, the sunflower seed oil is present in an amount of about 40% to about 60% w/w of the composition and the olive oil is present in an amount of about 1% to about 10% w/w of the composition. In some embodiments, the sunflower seed oil is present in an amount of about 65% w/w of the composition and the olive oil is present in an amount of about 5% w/w of the composition.

In some embodiments, the pharmaceutically acceptable base comprises a pharmaceutically acceptable wax. In some embodiments, the composition comprises about 1% to about 20% w/w of the composition of the pharmaceutically acceptable wax. For example, about 1% to about 10% w/w of the composition, about 10% to about 20% w/w of the composition, about 5% to about 15% w/w of the composition, or about 8% to 12% w/w of the composition of the pharmaceutically acceptable wax. In some embodiments, the composition comprises about 1% w/w of the composition, about 5% w/w of the composition, about 8% w/w of the composition, about 10% w/w of the composition, about 12% w/w of the composition, about 15% w/w of the composition, or about 20% w/w of the composition of the pharmaceutically acceptable wax.

In some embodiments, the pharmaceutically acceptable wax is present in an amount of about 1% to about 20% w/w of the composition. For example, about 1% to about 10% w/w of the composition, about 10% to about 20% w/w of the composition, about 5% to about 15% w/w of the composition, or about 8% to 12% w/w of the composition. In some embodiments, the pharmaceutically acceptable wax is present in an amount of the composition comprises about 1% w/w of the composition, about 5% w/w of the composition, about 8% w/w of the composition, about 10% w/w of the composition, about 12% w/w of the composition, about 15% w/w of the composition, or about 20% w/w of the composition.

In some embodiments, the pharmaceutically acceptable wax comprises beeswax, candelilla wax, cotton wax, carnauba wax, bayberry wax, insect wax (wax secreted by Ericerus pela), spermaceti, montan wax, bran wax, lanolin, capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, POE hydrogenated lanolin alcohol ethers, or a combination thereof.

In some embodiments, the pharmaceutically acceptable wax is selected from the group consisting of: beeswax, candelilla wax, cotton wax, carnauba wax, bayberry wax, insect wax (wax secreted by Ericerus pela), spermaceti, montan wax, bran wax, lanolin, capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, POE hydrogenated lanolin alcohol ethers, and a combination thereof.

In some embodiments, the pharmaceutically acceptable wax comprises beeswax. In some embodiments, the composition comprises about 1% to about 20% w/w of the composition of the beeswax. For example, about 1% to about 10% w/w of the composition, about 10% to about 20% w/w of the composition, about 5% to about 15% w/w of the composition, or about 8% to 12% w/w of the composition of the beeswax. In some embodiments, the composition comprises about 1% w/w of the composition, about 5% w/w of the composition, about 8% w/w of the composition, about 10% w/w of the composition, about 12% w/w of the composition, about 15% w/w of the composition, or about 20% w/w of the composition of the beeswax.

In some embodiments, the pharmaceutically acceptable wax is beeswax. In some embodiments, the beeswax is present in an amount of about 1% to about 20% w/w of the composition. For example, about 1% to about 10% w/w of the composition, about 10% to about 20% w/w of the composition, about 5% to about 15% w/w of the composition, or about 8% to about 12% w/w of the composition. In some embodiments, the beeswax is present in an amount of about 1% w/w of the composition, about 5% w/w of the composition, about 8% w/w of the composition, about 10% w/w of the composition, about 12% w/w of the composition, about 15% w/w of the composition, or about 20% w/w of the composition.

In some embodiments, the pharmaceutically acceptable base comprises a pharmaceutically acceptable oil and a pharmaceutically acceptable wax. In some embodiments, the composition comprises about 35% to about 85% w/w of the composition of the pharmaceutically acceptable oil and about 1% to about 20% w/w of the composition of the pharmaceutically acceptable wax. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition of the pharmaceutically acceptable oil and about 1% to about 10% w/w of the composition, about 10% to about 20% w/w of the composition, about 5% to about 15% w/w of the composition, or about 8% to 12% w/w of the composition of the pharmaceutically acceptable wax. In some embodiments, the composition comprises about 50% to about 60% w/w of the composition, about 45% to about 55% w/w of the composition, or about 55% to about 65% w/w of the composition of the pharmaceutically acceptable oil and about 5% to about 15% w/w of the composition of the pharmaceutically acceptable base. In some embodiments, the composition comprises about 40% w/w of the composition, about 45% w/w of the composition, about 50% w/w of the composition, about 55% w/w of the composition, about 60% w/w of the composition, about 65% w/w of the composition, or about 70% w/w of the composition of the pharmaceutically acceptable oil and about 1% w/w of the composition, about 5% w/w of the composition, about 8% w/w of the composition, about 10% w/w of the composition, about 12% w/w of the composition, about 15% w/w of the composition, or about 20% w/w of the composition of the pharmaceutically acceptable wax.

In some embodiments, the pharmaceutically acceptable base is a pharmaceutically acceptable oil and a pharmaceutically acceptable wax. In some embodiments, the pharmaceutically acceptable oil is present in an amount of about 35% to about 85% w/w of the composition and the pharmaceutically acceptable wax is present in an amount of about 1% to about 20% w/w of the composition. For example, the pharmaceutically acceptable oil is present in an amount of about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition and the pharmaceutically acceptable was is present in an amount of about 1% to about 10% w/w of the composition, about 10% to about 20% w/w of the composition, about 5% to about 15% w/w of the composition, or about 8% to 12% w/w of the composition. In some embodiments, the pharmaceutically acceptable oil is present in an amount of about 50% to about 60% w/w of the composition, about 45% to about 55% w/w of the composition, or about 55% to about 65% w/w of the composition and the pharmaceutically acceptable wax is present in an amount of about 5% to about 15% w/w of the composition. In some embodiments, the pharmaceutically acceptable oil is present in an amount of about 40% w/w of the composition, about 45% w/w of the composition, about 50% w/w of the composition, about 55% w/w of the composition, about 60% w/w of the composition, about 65% w/w of the composition, or about 70% w/w of the composition and the pharmaceutically acceptable wax is present in an amount of about 1% w/w of the composition, about 5% w/w of the composition, about 8% w/w of the composition, about 10% w/w of the composition, about 12% w/w of the composition, about 15% w/w of the composition, or about 20% w/w of the composition.

In some embodiments, the pharmaceutically acceptable oil comprises a plant oil. In some embodiments, the plant oil comprises avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, ojon oil, andiroba oil, tucuma oil, or a combination thereof.

In some embodiments, the pharmaceutically acceptable oil is a plant oil. In some embodiments, the plant oil is selected from the group consisting of: avocado oil, olive oil, sunflower seed oil, soybean oil, cottonseed oil, palm oil, palm kernel oil, linseed oil, almond oil, castor oil, corn oil, rapeseed oil, sesame oil, safflower oil, wheat germ oil, peach kernel oil, macadamia nut oil, apricot kernel oil, sasanqua oil, Perilla oil, peanut oil, tea seed oil, Torreya nucifera oil, rice-bran oil, jojoba oil, sea buckthorn oil, hemp oil, flaxseed oil, walnut oil, tea tree oil, evening primrose oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, sandalwood oil, spearmint oil, spikenard oil, vetiver oil, wintergreen oil, ylang ylang, bruiti oil, bacaba oil, acai oil, ojon oil, andiroba oil, tucuma oil, and a combination thereof.

In some embodiments, the pharmaceutically acceptable oil comprises triglycerides. In some embodiments, the triglycerides are of animal or vegetable origin or a combination thereof. In some embodiments, the triglycerides are natural, synthetic, or a combination thereof. In some embodiments, the triglycerides are medium chain triglycerides, mono-, di- and/or triglycerides, or mixtures thereof. Exemplary oils comprising triglycerides include, but are not limited to, sunflower seed oil, olive oil, castor oil, citrate triisocetyl triglycerides having 10-18 carbon atoms, caprylic/capric triglycerides (e.g., Myritol® 318), and egg yolk oil.

In some embodiments, the pharmaceutically acceptable oil comprises an animal oil. In some embodiments, the animal oil is selected from the group consisting of: mink oil, egg yolk oil, fish oil, turtle oil, lanolin, cod liver oil, crocodile oil, emu oil, horse oil, squalene oil, shark liver oil, tallow, or a combination thereof.

In some embodiments, the pharmaceutically acceptable oil is an animal oil. In some embodiments, the animal oil is selected from the group consisting of: mink oil, egg yolk oil, fish oil, turtle oil, lanolin, cod liver oil, crocodile oil, emu oil, horse oil, squalene oil, shark liver oil, tallow, and a combination thereof.

In some embodiments, the pharmaceutically acceptable oil comprises a synthetic oil. In some embodiments, the synthetic oil comprises isopropyl palmitate, etherified oils (e.g., dicaprylether, octyldodecanol), silicone oils (e.g., dimethicone oil, cyclomethicone), propoxylated fatty alcohols, capric/caprylic triglycerides (e.g., Myritol® 318), triolein, and tristearin glyceryl dilaurate, or a combination thereof.

In some embodiments, the pharmaceutically acceptable oil is a synthetic oil. In some embodiments, the synthetic oil is selected from the group consisting of: isopropyl palmitate, etherified oils (e.g., dicaprylether, octyldodecanol), silicone oils (e.g., dimethicone oil, cyclomethicone), propoxylated fatty alcohols, capric/caprylic triglycerides (e.g., Myritol® 318), triolein, and tristearin glyceryl dilaurate, and a combination thereof.

In some embodiments, the pharmaceutically acceptable wax comprises beeswax, candelilla wax, cotton wax, carnauba wax, bayberry wax, insect wax (wax secreted by Ericerus pela), spermaceti, montan wax, bran wax, lanolin, capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, POE hydrogenated lanolin alcohol ethers, or a combination thereof.

In some embodiments, the pharmaceutically acceptable wax is selected from the group consisting of: beeswax, candelilla wax, cotton wax, carnauba wax, bayberry wax, insect wax (wax secreted by Ericerus pela), spermaceti, montan wax, bran wax, lanolin, capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, microcrystalline wax, paraffin wax, POE lanolin alcohol ethers, POE lanolin alcohol acetates, POE cholesterol ethers, esters of lanolin fatty acids and polyethylene glycol, fatty acid glycerides, hydrogenated castor oil, petrolatum, POE hydrogenated lanolin alcohol ethers, and a combination thereof.

In some embodiments, the pharmaceutically acceptable base comprises a pharmaceutically acceptable oil and a pharmaceutically acceptable wax. In some embodiments, the pharmaceutically acceptable base comprises sunflower seed oil, olive oil, and beeswax. In some embodiments, the composition comprises about 35% to about 85% w/w of the composition of the sunflower seed oil and olive oil and about 1% to about 20% w/w of the composition of the beeswax. For example, about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition of the sunflower seed oil and olive oil and about 1% to about 10% w/w of the composition, about 10% to about 20% w/w of the composition, about 5% to about 15% w/w of the composition, or about 8% to 12% w/w of the composition of the beeswax. In some embodiments, the composition comprises about 50% to about 60% w/w of the composition, about 45% to about 55% w/w of the composition, or about 55% to about 65% w/w of the composition of the sunflower seed oil and olive oil and about 5% to about 15% w/w of the composition of the beeswax. In some embodiments, the composition comprises about 40% w/w of the composition, about 45% w/w of the composition, about 50% w/w of the composition, about 55% w/w of the composition, about 60% w/w of the composition, about 65% w/w of the composition, or about 70% w/w of the composition of the sunflower seed oil and olive oil and about 1% w/w of the composition, about 5% w/w of the composition, about 8% w/w of the composition, about 10% w/w of the composition, about 12% w/w of the composition, about 15% w/w of the composition, or about 20% w/w of the composition of the beeswax. In some embodiments, the composition comprises about 40% to about 60% w/w of the composition of the sunflower seed oil, about 1% to about 10% w/w of the composition of the olive oil, and about 5% to about 15% of the beeswax. In some embodiments, the composition comprises about 50% w/w of the composition of the sunflower seed oil, about 5% w/w of the composition of the olive oil, and about 10% w/w of the composition of the beeswax.

In some embodiments, the pharmaceutically acceptable base is pharmaceutically acceptable oil and a pharmaceutically acceptable wax. In some embodiments, the pharmaceutically acceptable base is sunflower seed oil, olive oil, and beeswax. In some embodiments, the sunflower seed oil and olive oil are present in an amount of about 35% to about 85% w/w of the composition and the beeswax is present in an amount of about 1% to about 20% w/w of the composition. For example, the sunflower seed oil and olive oil are present in an amount of about 35% to about 55% w/w of the composition, about 35% to about 60% w/w of the composition, about 50% to about 85% w/w of the composition, about 45% to about 85% w/w of the composition, about 55% to about 85% of the composition, about 35% to about 75% w/w of the composition, about 45% to about 65% w/w of the composition, or about 40% to about 60% w/w of the composition and the beeswax is present in an amount of about 1% to about 10% w/w of the composition, about 10% to about 20% w/w of the composition, about 5% to about 15% w/w of the composition, or about 8% to 12% w/w of the composition. In some embodiments, the sunflower seed oil and olive oil are present in an amount of about 40% to about 60% w/w of the composition and the beeswax is present in an amount of 1% to about 10% w/w of the composition. In some embodiments, the sunflower seed oil and olive oil are present in an amount of about 40% w/w of the composition, about 45% w/w of the composition, about 50% w/w of the composition, about 55% w/w of the composition, about 60% w/w of the composition, about 65% w/w of the composition, or about 70% w/w of the composition and the beeswax is present in an amount of about 1% w/w of the composition, about 5% w/w of the composition, about 8% w/w of the composition, about 10% w/w of the composition, about 12% w/w of the composition, about 15% w/w of the composition, or about 20% w/w of the composition. In some embodiments, the sunflower seed oil is present in an amount of about 40% to about 60% w/w of the composition, the olive oil is present in an amount of about 1% to about 10% w/w of the composition, and the beeswax is present in an amount of about 5% to about 15% w/w of the composition. In some embodiments, the sunflower seed oil is present in an amount of about 50% w/w of the composition, the olive oil is present in an amount of about 5% w/w of the composition, and the beeswax is present in an amount of about 10% of the composition.

In some embodiments, the pharmaceutically acceptable base comprises a pharmaceutically acceptable butter. In some embodiments, the composition comprises about 0.005% w/w to about 1% w/w of the composition of the pharmaceutically acceptable butter. For example, from about 0.005% w/w to about 0.01% w/w of the composition, from about 0.005% w/w to about 0.02% w/w of the composition, from about 0.005% w/w to about 0.03% w/w of the composition, from about 0.005% w/w to about 0.05% w/w of the composition, from about 0.005% w/w to about 0.1% w/w of the composition, from about 0.005% w/w to about 0.5% w/w of the composition, from about 0.01% w/w to about 1% w/w of the composition, from about 0.05% w/w to about 1% w/w of the composition, from about 0.1% w/w to about 1% w/w of the composition, from about 0.005% w/w to about 0.05% w/w of the composition, from about 0.005% w/w to about 0.015% w/w of the composition, or from about 0.005% w/w to about 0.01% of the composition of the pharmaceutically acceptable butter. In some embodiments, the composition comprises about 0.005% w/w of the composition, about 0.007% w/w of the composition, about 0.008% w/w of the composition, about 0.01% w/w of the composition, about 0.012% w/w of the composition, about 0.015% w/w of the composition, about 0.02% w/w of the composition, about 0.03% w/w of the composition, about 0.04% w/w of the composition, about 0.05% w/w of the composition, or about 0.08% w/w of the composition of the pharmaceutically acceptable butter.

In some embodiments, the pharmaceutically acceptable base comprises a pharmaceutically acceptable butter. In some embodiments, the pharmaceutically acceptable butter is present in an amount of about 0.005% w/w to about 1% w/w of the composition. For example, from about 0.005% w/w to about 0.01% w/w of the composition, from about 0.005% w/w to about 0.02% w/w of the composition, from about 0.005% w/w to about 0.03% w/w of the composition, from about 0.005% w/w to about 0.05% w/w of the composition, from about 0.005% w/w to about 0.1% w/w of the composition, from about 0.005% w/w to about 0.5% w/w of the composition, from about 0.01% w/w to about 1% w/w of the composition, from about 0.05% w/w to about 1% w/w of the composition, from about 0.1% w/w to about 1% w/w of the composition, from about 0.005% w/w to about 0.05% w/w of the composition, from about 0.005% w/w to about 0.015% w/w of the composition, or from about 0.005% w/w to about 0.01% of the composition. In some embodiments, the pharmaceutically acceptable butter is present in an amount of about 0.005% w/w of the composition, about 0.007% w/w of the composition, about 0.008% w/w of the composition, about 0.01% w/w of the composition, about 0.012% w/w of the composition, about 0.015% w/w of the composition, about 0.02% w/w of the composition, about 0.03% w/w of the composition, about 0.04% w/w of the composition, about 0.05% w/w of the composition, or about 0.08% w/w of the composition.

In some embodiments, the pharmaceutically acceptable butter is selected form the group consisting of: shea butter, cocoa butter, illipe butter, mango butter, almond butter, kokum butter, sal butter, cupuacu butter, aloe butter, avocado butter, chaulmoogra butter, dhupu butter, hemp butter, kukui nut butter, macademia nut butter, jojoba butter, tucuma butter, or a combination thereof.

In some embodiments, the pharmaceutically acceptable base comprises a pharmaceutically acceptable butter. In some embodiments, the pharmaceutically acceptable butter comprises cocoa butter, shea butter, or a combination thereof. In some embodiments, the composition comprises about 0.005% w/w to about 0.01% w/w of the composition, from about 0.005% w/w to about 0.02% w/w of the composition, from about 0.005% w/w to about 0.03% w/w of the composition, from about 0.005% w/w to about 0.05% w/w of the composition, from about 0.005% w/w to about 0.1% w/w of the composition, from about 0.005% w/w to about 0.5% w/w of the composition, from about 0.01% w/w to about 1% w/w of the composition, from about 0.05% w/w to about 1% w/w of the composition, from about 0.1% w/w to about 1% w/w of the composition, from about 0.005% w/w to about 0.05% w/w of the composition, from about 0.005% w/w to about 0.015% w/w of the composition, or from about 0.005% w/w to about 0.01% of the composition of the shea butter, cocoa butter, or a combination thereof. In some embodiments, the composition comprises about 0.005% w/w of the composition, about 0.007% w/w of the composition, about 0.008% w/w of the composition, about 0.01% w/w of the composition, about 0.012% w/w of the composition, about 0.015% w/w of the composition, about 0.02% w/w of the composition, about 0.03% w/w of the composition, about 0.04% w/w of the composition, about 0.05% w/w of the composition, or about 0.08% w/w of the composition of the shea butter, cocoa butter, or a combination thereof.

In some embodiments, the pharmaceutically acceptable base comprises a pharmaceutically acceptable butter. In some embodiments, the pharmaceutically acceptable butter comprises shea butter, cocoa butter, or a combination thereof. In some embodiments, the shea butter, cocoa butter, or a combination thereof is present in an amount of about 0.005% w/w to about 1% w/w of the composition. For example, from about 0.005% w/w to about 0.01% w/w of the composition, from about 0.005% w/w to about 0.02% w/w of the composition, from about 0.005% w/w to about 0.03% w/w of the composition, from about 0.005% w/w to about 0.05% w/w of the composition, from about 0.005% w/w to about 0.1% w/w of the composition, from about 0.005% w/w to about 0.5% w/w of the composition, from about 0.01% w/w to about 1% w/w of the composition, from about 0.05% w/w to about 1% w/w of the composition, from about 0.1% w/w to about 1% w/w of the composition, from about 0.005% w/w to about 0.05% w/w of the composition, from about 0.005% w/w to about 0.015% w/w of the composition, or from about 0.005% w/w to about 0.01% of the composition. In some embodiments, the shea butter, cocoa butter, or a combination thereof is present in an amount of about 0.005% w/w of the composition, about 0.007% w/w of the composition, about 0.008% w/w of the composition, about 0.01% w/w of the composition, about 0.012% w/w of the composition, about 0.015% w/w of the composition, about 0.02% w/w of the composition, about 0.03% w/w of the composition, about 0.04% w/w of the composition, about 0.05% w/w of the composition, or about 0.08% w/w of the composition.

In some embodiments, a topical composition as provided herein further includes colloidal oatmeal. In some embodiments, the composition further comprises rosemary extract (e.g., Rosamox®), bisabolol, or a combination thereof. In some embodiments, the composition further includes oils such as lavender oil, tea tree oil, rosemary oil, peppermint oil, eucalyptus oil, or a combination thereof.

In some embodiments, a topical composition as provided herein comprises:
about 1% to about 10% w/w of the composition of a topical anesthetic, topical analgesic, or a combination thereof;
about 5% to about 50% w/w of the composition of a coating agent; and
about 1% to about 10% w/w of the composition of a vitamin B3 compound.

In some of the above embodiments, the composition further includes a pharmaceutically acceptable base, wherein the pharmaceutically acceptable base comprises a pharmaceutically acceptable oil, pharmaceutically acceptable wax, or a combination thereof, and the composition comprises about 35% to about 85% w/w of the composition of the pharmaceutically acceptable oil, about 1% to about 20% w/w of the composition of the pharmaceutically acceptable wax, or a combination thereof. In some embodiments, the pharmaceutically acceptable base further comprises a pharmaceutically acceptable butter, and the composition comprises about 0.005% w/w to about 0.02% w/w of the composition of the pharmaceutically acceptable butter. In some embodiments, the composition further comprises colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein comprises:
about 1% to about 10% w/w of the composition of a topical anesthetic, topical analgesic, or a combination thereof; and
about 5% to about 50% w/w of the composition of a coating agent.

In some embodiments, a topical composition as provided herein comprises:
about 1% to about 10% w/w of the composition of a topical anesthetic, topical analgesic, or a combination thereof; and
about 1% to about 10% w/w of the composition of a vitamin B3 compound.

In some embodiments, a topical composition as provided herein comprises:
about 5% to about 50% w/w of the composition of a coating agent; and
about 1% to about 10% w/w of the composition of a vitamin B3 compound.

In some of the above embodiments, the composition further includes a pharmaceutically acceptable base, wherein the pharmaceutically acceptable base comprises a pharmaceutically acceptable oil, pharmaceutically acceptable wax, or a combination thereof, and the composition comprises about 35% to about 85% w/w of the composition of the pharmaceutically acceptable oil, about 1% to about 20% w/w of the composition of the pharmaceutically acceptable wax, or a combination thereof. In some embodiments, the pharmaceutically acceptable base further comprises a pharmaceutically acceptable butter, and the composition comprises about 0.005% w/w to about 0.02% w/w of the composition of the pharmaceutically acceptable butter. In some embodiments, the composition further comprises colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein includes:
a topical anesthetic, topical analgesic, or a combination thereof present in an amount of about 1% to about 10% w/w of the composition;
a coating agent present in an amount of about 5% to about 50% w/w of the composition of; and
a vitamin B3 compound present in an amount of about 1% to about 10% w/w of the composition.

In some of the above embodiments, the composition further includes a pharmaceutically acceptable base, wherein the pharmaceutically acceptable base is a pharmaceutically acceptable oil, pharmaceutically acceptable wax, or a combination thereof, and the pharmaceutically acceptable oil is present in an amount of about 35% to about 85% w/w of the composition of the pharmaceutically acceptable oil and the pharmaceutically acceptable wax is present in an amount of about 1% to about 20% w/w of the composition. In some embodiments, the pharmaceutically acceptable base further includes a pharmaceutically acceptable butter, and the pharmaceutically acceptable butter is present in an amount of about 0.005% w/w to about 0.02% w/w of the composition. In some embodiments, the composition further includes colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein comprises:
about 5% w/w of the composition of a topical anesthetic, topical analgesic, or a combination thereof;
about 25% w/w of the composition of a coating agent; and
about 5% w/w of the composition of a vitamin B3 compound.

In some of the above embodiments, the composition further comprises a pharmaceutically acceptable base, wherein the pharmaceutically acceptable base comprises a pharmaceutically acceptable oil, pharmaceutically acceptable wax, or a combination thereof, and the composition comprises about 55% w/w of the composition of the pharmaceutically acceptable oil, about 10% w/w of the composition of the pharmaceutically acceptable wax; or a combination thereof. In some embodiments, the pharmaceutically acceptable base further comprises a pharmaceutically acceptable butter, and the composition comprises about 0.02% w/w of the composition of the pharmaceutically acceptable butter. In some embodiments, the composition further comprises colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein comprises:
about 5% w/w of the composition of a topical anesthetic, topical analgesic, or a combination thereof; and
about 25% w/w of the composition of a coating agent.

In some embodiments, a topical composition as provided herein comprises:

about 5% w/w of the composition of a topical anesthetic, topical analgesic, or a combination thereof; and about 5% w/w of the composition of a vitamin B3 compound.

In some embodiments, a topical composition as provided herein comprises:

about 25% w/w of the composition of a coating agent; and about 5% w/w of the composition of a vitamin B3 compound.

In some of the above embodiments, the composition further comprises a pharmaceutically acceptable base, wherein the pharmaceutically acceptable base comprises a pharmaceutically acceptable oil, pharmaceutically acceptable wax, or a combination thereof, and the composition comprises about 55% w/w of the composition of the pharmaceutically acceptable oil, about 10% w/w of the composition of the pharmaceutically acceptable wax; or a combination thereof. In some embodiments, the pharmaceutically acceptable base further comprises a pharmaceutically acceptable butter, and the composition comprises about 0.02% w/w of the composition of the pharmaceutically acceptable butter. In some embodiments, the composition further comprises colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein includes:

a topical anesthetic, topical analgesic, or a combination thereof present in an amount of about 5% w/w of the composition;

a coating agent present in an amount of about 25% w/w of the composition; and a vitamin B3 compound present in an amount of about 5% w/w of the composition of.

In some of the above embodiments, the composition further includes a pharmaceutically acceptable base, wherein the pharmaceutically acceptable base is a pharmaceutically acceptable oil, pharmaceutically acceptable wax, or a combination thereof, and the pharmaceutically acceptable oil is present in an amount of about 55% w/w of the composition, and the pharmaceutically acceptable wax is present in an amount of about 10% w/w of the composition. In some embodiments, the pharmaceutically acceptable base further includes a pharmaceutically acceptable butter, and the pharmaceutically acceptable butter is present in an amount of about 0.02% w/w of the composition. In some embodiments, the composition further includes colloidal oatmeal, rosemary extract (e.g., Rosamox®), bisabolol, lavender oil, tea tree oil, rosemary oil, peppermint oil, eucalyptus oil, or a combination thereof.

In some embodiments, the topical anesthetic is lidocaine; the vitamin B3 compound is niacinamide; and the coating agent is zinc oxide. For example, a topical composition as provided herein can comprise:

about 1% to about 10% w/w of the composition of lidocaine;

about 5% to about 50% w/w of the composition of zinc oxide; and about 1% to about 10% w/w of the composition of niacinamide.

In some embodiments, a topical composition as provided herein includes:

about 1% to about 10% w/w of the composition of lidocaine; and about 5% to about 50% w/w of the composition of zinc oxide.

In some embodiments, a topical composition as provided herein includes:

about 1% to about 10% w/w of the composition of lidocaine; and about 1% to about 10% w/w of the composition of niacinamide.

In some embodiments, a topical composition as provided herein includes:

about 5% to about 50% w/w of the composition of zinc oxide; and about 5% to about 50% w/w of the composition of niacinamide.

In some of the above embodiments, the composition further comprises an analgesic. In some embodiments, the composition further includes a pharmaceutically acceptable base comprising sunflower seed oil, olive oil, beeswax, or a combination thereof. In some of the above embodiments, the composition comprises olive oil and sunflower seed oil at about 55% w/w of the composition, beeswax at about 10% w/w of the composition, or a combination thereof. In some embodiments, the pharmaceutically acceptable base further comprises a pharmaceutically acceptable butter, and the composition comprises about 0.005% w/w to about 0.02% w/w of the composition of the pharmaceutically acceptable butter. In some embodiments, the composition further comprises colloidal oatmeal, rosemary extract (e.g., Rosamox®), bisabolol, lavender oil, tea tree oil, rosemary oil, peppermint oil, eucalyptus oil, or a combination thereof.

In some embodiments, the topical anesthetic is lidocaine; the vitamin B3 compound is niacinamide; and the coating agent is zinc oxide. For example, a topical composition as provided herein can include:

lidocaine present in an amount of about 1% to about 10% w/w of the composition;

zinc oxide present in amount of about 5% to about 50% w/w of the composition; and niacinamide present in an amount of about 1% to about 10% w/w of the composition.

In some embodiments, a topical composition as provided herein includes:

lidocaine present in an amount of about 1% to about 10% w/w of the composition; and zinc oxide present in an amount of about 5% to about 50% w/w of the composition.

In some embodiments, a topical composition as provided herein includes:

lidocaine present in an amount of about 1% to about 10% w/w of the composition; and niacinamide present in an amount of about 1% to about 10% w/w of the composition.

In some embodiments, a topical composition as provided herein includes:

zinc oxide present in an amount of about 5% to about 50% w/w of the composition; and niacinamide present in an amount of about 1% to about 10% w/w of the composition.

In some of the above embodiments, the composition further includes an analgesic. In some embodiments, the composition further includes a pharmaceutically acceptable base, and the pharmaceutically acceptable base is sunflower seed oil, olive oil, beeswax, or a combination thereof. In some embodiments, the olive oil and sunflower seed oil are present in an amount of about 55% w/w of the composition and the beeswax is present in an amount of about 10% w/w of the composition. In some embodiments, the pharmaceutically acceptable base further includes a pharmaceutically acceptable butter is present in an amount of about 0.005% w/w to about 0.02% w/w of the composition. In some embodiments, the composition further includes colloidal oatmeal, rosemary extract (e.g., Rosamox®), bisabolol, lavender oil, tea tree oil, rosemary oil, peppermint oil, eucalyptus oil, or a combination thereof.

As another example, a topical composition as provided herein comprises:
    about 5% w/w of the composition of lidocaine;
    about 25% w/w of the composition of zinc oxide; and
    about 5% w/w of the composition of niacinamide.

In some embodiments, a topical composition as provided herein comprises:
    about 5% w/w of the composition of lidocaine; and
    about 25% w/w of the composition of zinc oxide.

In some embodiments, a topical composition as provided herein comprises:
    about 5% w/w of the composition of lidocaine; and
    about 5% w/w of the composition of niacinamide.

In some embodiments, a topical composition as provided herein comprises:
    about 25% w/w of the composition of zinc oxide; and
    about 5% w/w of the composition of niacinamide.

In some of the above embodiments, the composition further comprises an analgesic. In some embodiments, the composition further comprises a pharmaceutically acceptable base comprising sunflower seed oil, olive oil, beeswax, or a combination thereof and the composition comprises about 55% w/w of the composition of the olive oil and sunflower seed oil, about 15% w/w of the composition of the beeswax, or a combination thereof. In some embodiments, the sunflower seed oil is present in an amount of about 50% w/w of the composition. In some embodiments, the olive oil is present in an amount of about 5% w/w of the composition. In some embodiments, the pharmaceutically acceptable base further includes a pharmaceutically acceptable butter, and the pharmaceutically acceptable butter is present in an amount of about 0.005% w/w to about 0.02% w/w of the composition. In some embodiments, the composition further includes colloidal oatmeal, rosemary extract (e.g., Rosamox®), bisabolol, lavender oil, tea tree oil, rosemary oil, peppermint oil, eucalyptus oil, or a combination thereof.

As another example, a topical composition as provided herein includes:
    lidocaine present in an amount of about 5% w/w of the composition;
    zinc oxide present in an amount of about 25% w/w of the composition; and
    niacinamide present in an amount about 5% w/w of the composition.

In some of the above embodiments, the composition further comprises an analgesic. In some embodiments, the composition further includes a pharmaceutically acceptable base, and the pharmaceutically acceptable base is sunflower seed oil, olive oil, beeswax, or a combination thereof. In some embodiments, the olive oil and sunflower seed oil are present in an amount of about 55% w/w of the composition, and the beeswax is present in an amount of about 15% w/w of the composition. In some embodiments, the sunflower seed oil is present in an amount of about 50% w/w of the composition. In some embodiments, the olive oil is present in an amount of about 5% w/w of the composition. In some embodiments, the pharmaceutically acceptable base further includes a pharmaceutically acceptable butter, and the pharmaceutically acceptable butter is present in an amount of about 0.02% w/w of the composition. In some embodiments, the composition further includes colloidal oatmeal, rosemary extract (e.g., Rosamox®), bisabolol, lavender oil, tea tree oil, rosemary oil, peppermint oil, eucalyptus oil, or a combination thereof.

In some embodiments, a topical composition as provided herein comprises:
    about 25% to about 75% w/w sunflower seed oil;
    about 1% to about 10% w/w olive oil;
    about 1% to about 10% w/w lidocaine;
    about 5% to about 50% w/w zinc oxide;
    about 1% to about 10% w/w niacinamide; and
    about 1% to about 20% w/w beeswax.

In some embodiments, a topical composition as provided herein is:
    about 25% to about 75% w/w sunflower seed oil;
    about 1% to about 10% w/w olive oil;
    about 1% to about 10% w/w lidocaine;
    about 5% to about 50% w/w zinc oxide;
    about 1% to about 10% w/w niacinamide; and
    about 1% to about 20% w/w beeswax.

In some embodiments, a topical composition as provided herein is:
    about 50% w/w sunflower seed oil;
    about 5% w/w olive oil;
    about 5% w/w lidocaine;
    about 25% w/w zinc oxide;
    about 5% w/w niacinamide; and
    about 10% w/w beeswax.

In some embodiments, the composition includes at least one carrier, diluent, excipient, or a combination thereof. In some embodiments, the composition is in the form of a paste, gel, cream, spray, suppository, mousse, emollient, ointment, foam, or suspension.

Methods of Use

Provided herein are methods of treating pruritus ani in a subject in need thereof, the method comprising administering to the subject a therapeutically effective amount of a composition from a topical composition provided herein. In some embodiments, the subject is an infant, a child, an adolescent, or an elderly subject.

In some embodiments, administration of a provided topical composition reduces the anal itch in the subject to which it is administered.

In some embodiments, provided herein are methods for treating pruritus ani in a subject. In some embodiments, the pruritus ani is associated with one or more of the following: diarrhea, rectal incontinence, stool leakage, parasitic infections of the GI tract, excess anal moisture, excess anal perspiration, fungal overgrowth in the anal region, psoriasis, Crohn's disease, hemorrhoids, anal fissures, bacterial skin infections, viral infections (e.g., anal warts), seborrheic dermatitis, atopic dermatitis, contact dermatitis, lichen planus, lichen simplex, lichen sclerosis, diabetes mellitus, leukemia and lymphoma, kidney failure, liver diseases (obstructive jaundice), iron deficiency anemia, and hyperthyroidism.

In some embodiments, provided herein are methods for reducing anal itch in a subject. In some embodiments, the anal itch is associated with one or more of the following: diarrhea, rectal incontinence, stool leakage, parasitic infections of the GI tract, excess anal moisture, excess anal perspiration, fungal overgrowth in the anal region, psoriasis, Crohn's disease, hemorrhoids, anal fissures, bacterial skin infections, viral infections (e.g., anal warts), seborrheic dermatitis, atopic dermatitis, contact dermatitis, lichen planus, lichen simplex, lichen sclerosis, diabetes mellitus, leukemia and lymphoma, kidney failure, liver diseases (obstructive jaundice), iron deficiency anemia, or hyperthyroidism.

In some embodiments, provided herein is the use of a topical composition as provided herein to treat pruritus ani in a subject by topically administering to the subject in need thereof.

In some embodiments, provided herein is the use of a topical composition as provided herein in the manufacture of a medicament for reducing anal itch.

Also provided herein are methods for reducing itching in a subject in need thereof, the method comprising administering to the subject a therapeutically effective amount of the composition as provided herein. In some embodiments, at least a portion of the skin of the subject itches. In some embodiments, the itching on the subject is located on the head, an arm, torso, a leg, neck, a hand, or a foot of the subject. In some embodiments, the subject is an infant, a child, an adolescent, or an elderly subject.

In some embodiments, the topical compositions can be applied in a single, one-time application, once a week, once a bi-week, once a month, from one to four times daily, or from one to three times daily, or from one to two times daily, or for a period of time sufficient to alleviate symptoms or treat the pruritus ani. For example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. The topical compositions provided herein can be administered, for example, at a frequency of once per day, twice per day, three times per day, or four times per day. The topical compositions provided herein can be topically administered once or twice per day for a period of time from 1 week to 12 weeks, from 1 week to 4 weeks, for 1 week, for 2 weeks, for 3 weeks, for 4 weeks, for 5 weeks, for 6 weeks, for 7 weeks, for 8 weeks, for 9 weeks, for 10 weeks, for 11 weeks, or for 12 weeks.

In some embodiments, after an initial treatment period of a few days of daily or twice daily application, the topical compositions could be used less frequently than daily or twice daily.

In some embodiments, after an initial treatment period of one week of daily or twice daily application, the topical compositions could be used less frequently than daily or twice daily.

In some embodiments, after an initial treatment period of two weeks of daily or twice daily application, the topical compositions could be used less frequently than daily or twice daily.

The provided topical compositions as provided herein can be applied in a therapeutically effective amount, for example, an amount sufficient to cover an affected area plus a margin of healthy skin or tissue surrounding the affected area, for example, a margin of about 0.5 inches.

In some embodiments, a topical composition as provided herein is applied at a frequency of from one to four times daily, including for example, once daily, twice daily, three times daily, or four times daily, for a period of time sufficient to alleviate symptoms or treat the pruritus ani. For example, for a period of time from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, or for 52 weeks. For example, the provided compositions can be topically administered at a frequency of once per day for a period of time from 1 week to 52 weeks, for example for about from 24 weeks to 48 weeks. In some embodiments, the provided compositions can be topically administered at a frequency of twice per day for a period of time from 1 week to 24 weeks, for example for about from 1 week to 12 weeks, such as for about 1 week to 4 weeks or about 1 week to 3 weeks. In some embodiments, the provided compositions can be topically administered at a frequency of thrice per day for a period of time from 1 week to 24 weeks, for example for about from 1 week to 12 weeks, such as for about 1 week to 4 weeks. In some embodiments, the provided compositions can be topically administered at a frequency of twice per day for a period of time from about 1 week to 4 weeks, for example for about from 1 week to 3 weeks, such as for about 1 week to 2 weeks.

In some embodiments, a topical composition as provided herein is applied at a frequency of from one to four times daily, including for example, once daily, twice daily, three times daily, or four times daily, for a period of time sufficient to alleviate symptoms or treat the pruritus ani. For example, for a period of time of about 1 week, about 2 weeks, about 3 weeks, or about 4 weeks. In some embodiments, a topical composition as provided herein is applied at a frequency of twice daily for 2 weeks.

EXAMPLES

The invention will be described in greater detail by way of specific examples. The following examples are offered for illustrative purposes, and to exemplify the topical compositions and methods described herein and are not intended to limit the invention in any manner. Many variations will suggest themselves and are within the full intended scope. Those of skill in the art will readily recognize a variety of non-critical parameters that can be changed or modified to yield essentially the same results.

Example 1

Pruritus Ani Composition

Materials

Table 1—Exemplary possible ingredients suitable for the production of topical compositions disclosed herein.

TABLE 1

Exemplary Possible Ingredients Suitable for the Production of Topical Compositions

| Ingredients | % w/w | Amount (g) |
|---|---|---|
| Organic sunflower seed oil | 50.00 | 250.00 |
| Olive oil | 5.00 | 25.00 |
| Niacinamide | 5.00 | 25.00 |
| Beeswax granules | 10.00 | 50.00 |
| Zinc oxide | 25.00 | 125.00 |
| Lidocaine | 5.00 | 25.00 |

Preparation

The sunflower seed oil was added to the tank, and the olive oil was added with mixing to the sunflower seed oil. The sunflower seed oil and olive oil were mixed until homogeneous. The niacinamide was added slowly with constant mixing. The particle size of the niacinamide was reduced to submicron levels so that no graininess was detectable. The particle size was reduced by recirculating the composition through a high-sheer homogenizer. The temperature was kept below 75° C. throughout the particle size reduction process. With mixing, the zinc oxide was added slowly to the composition. The particle size of the zinc oxide was also reduced to submicron levels so that no graininess was detectable. The particle size was reduced by recirculating the composition through a high-sheer homogenizer, and the temperature was kept below 75° C. throughout the process. Once the particle size was reduced, the beeswax was added with vigorous mixing. With constant mixing, the composition was then heated to 75° C. and maintained at 75° C. until all of the beeswax melted and the composition was homogenous. The composition was slowly cooled to 65° C. with constant mixing to avoid the composition solidifying on the sides of the tank. It is very important that sweep mixing is constant throughout this step. At 65° C., the lidocaine was slowly added, and the composition was mixed until uniform. The particle size was reduced again until no graininess was detectable. The composition was then cooled to 36-38° C. with constant mixing and side-sweep mixing. It is very important that sweep mixing is constant throughout this step. The temperature of the composition was maintained at 36-38° C. with mixing while filling.

Example 2

Pruritus Ani Composition Assay

Internal Standard Solution Preparation

About 0.4 g of benzyl benzoate was transferred into a 100 mL volumetric flask, diluted to volume with 100% isopropyl alcohol, and mixed. The amount of benzyl benzoate was recorded to the nearest 0.1 mg.

Reference Standard Solution Preparation

About 100 mg of lidocaine and 100 mg of niacinamide were added to a 100 mL volumetric flask. The amounts of the lidocaine and niacinamide were recorded to the nearest 0.1 mg. 25.0 mL of the above internal standard solution was added to the volumetric flask with the lidocaine and niacinamide using a Class "A" 25.0 mL volumetric pipette. The solution was diluted to 100 mL with 100% isopropyl alcohol and mixed well.

Test Solution Preparation

About 2.0 g of the finished pruritus ani composition was added to a 100 mL volumetric flask. 25.0 mL of the above internal standard solution was added to the volumetric flask with the finished pruritus ani composition using a Class "A" 25.0 mL volumetric pipette. The solution was mixed well. About 50 mL of isopropyl alcohol was added to the flask, and the solution was heated with constant mixing until the composition was fully melted. Isopropyl alcohol was added to the flask to 100 mL mark, and the solution was cooled to room temperature. Isopropyl alcohol was again added to the 100 mL mark, and the solution was mixed thoroughly. Undissolved materials were allowed to settle, and the solution from the top of the flask was filtered through a 0.45 μm nylon syringe filter into a gas chromatography vial.

Gas Chromatography

The column was a Supelco Equity-5 with a length of 30 m, a diameter of 0.53 mm, and a film thickness of 0.5 μm. The column was coated with 5% diphenyl/95% dimethyl polysiloxane. The oven was initially set to a temperature of 200° C. and kept at 200° C. for the total run time of 10 minutes. The conditions were as follows: the carrier gas was helium, the linear velocity was set to 35 cm/s, the split ratio was set to 10:1, the split mode was set to split, and the control mode was set to "press". The injector temperature was 250° C. and the detector temperature was 300° C. An injection volume of 1.0 μL was employed using an auto-injector.

The Reference Standard Solution and Test solution were each injected three times. The retention times for the niacinamide, benzyl benzoate, and lidocaine were 2.4 minutes, 4.4 minutes, and 6.1 minutes, respectively.

Example 3

Study of an Ointment to Heal Rectal Itch

Patient Population

Any patient, male or female, age 18-90, presenting with pruritus ani in need of treatment was eligible for the study. Only those individuals satisfying the inclusion and exclusion criteria presented below participated.

Inclusion Criteria:
1. Documented pruritus ani.
2. Male or female.
3. Age 18-90.
4. Willing to participate and capable of understanding the clinical study procedure and give informed consent.
5. Anorectal itch lasting more than 2 weeks.
6. Compatible physical exam.

Exclusion Criteria:
1. Unable to understand informed consent.
2. Inflammatory bowel disease, known venereal disease, immunodeficiency disease.
3. Anal/perianal abscess.
4. Anal or rectal surgery within the past 12 weeks.
5. Pregnancy or breastfeeding female.
6. Signs of other rectal diseases such as, anorectal fistula, infection, perianal eczema or tumors.

Protocol

Patients presenting with pruritus ani were assessed in the standard manner per usual care. A standard history was taken including current symptoms, past medical history including diarrhea, constipation, fecal incontinence, antibiotic use, inflammatory bowel disease, previous pregnancies and any previous ano-rectal surgery, social history, and medication usage including use of any laxatives. A detailed physical exam was also performed including an ano-rectal exam to assess the pruritus ani. Detailed demographic information was also captured from each patient specific to pruritus ani. The patients were not randomized.

A visual exam of the ano-rectum was also carried out per standard practice including possible anoscopy, flexible sigmoidoscopy and/or colonoscopy.

There is no strict definition of pruritus ani, but in practice the presence the following symptoms or signs has been used:
a) persistent itch in the ano-rectal region;
b) consistent physical exam with erythema, inflammation and/or breaks in the anoderm. If pruritus ani was confirmed, informed consent was obtained for the study.

Patients in the study applied the pruritus ani composition as described in Example 1, in a prespecified amount (per packaged applicator), twice daily for about 1-2 weeks. In addition to the treatment, all patients were maintained on standard care for pruritus ani, including, but not limited to, a high-fiber diet, laxatives as needed and appropriate maintenance of the region of the anoderm by keeping the area clean and dry using non-soapy water and appropriate drying. Patients were followed in the office on an as needed basis, but were specifically assessed at 1-2 weeks, following diagnosis, either by phone or office visit.

Primary Efficacy Endpoint

The primary endpoint was the rate of improvement or resolution of symptoms (itch and discomfort) at 1-2 weeks. This was determined either in the office or by physician phone follow-up. At least 50% symptom improvement was necessary for a successful endpoint.

Statistical Analysis

Patients served as their own controls for statistical analysis. All analyses were performed via the intention-to-treat principle. A two-tailed, paired Student's t-test or the Wilcoxon signed rank test is used to assess the discrete variables. (Based on a 75% success rate for at least 50% symptom improvement using the pruritus ani composition, and assuming 30% improvement with no intervention, 20 patients would be required to have a 90% chance of detecting significance at the 5% level, so the study is adequately powered for the outcomes chosen.)

Results

Eleven patients were treated with the pruritus ani composition as described in this Example. Table 2 provides characteristics of the treated patients and shows the results of the treatment for each patient. In Table 2, the symptom scale is from 1 to 5, with 1 being the most bothersome symptoms and worst visual exam, and 5 being completely asymptomatic with a normal visual exam.

TABLE 2

Patient characteristics and results of anal itch treatment

| Patient Number* | Ethnicity | Weight | Initial Symptoms | Follow-up Symptoms | Initial Visual Exam | Follow Up Visual Exam |
|---|---|---|---|---|---|---|
| 001 | caucasian | 200 lb | 1 | 5 | 1 | n/a |
| 002 | caucasian | 148 lb | 2 | 5 | 2 | 5 |
| 003 | caucasian | 200 lb | 2 | 5 | 1 | 5 |
| 004 | caucasian | 182 lb | 1 | 5 | 1 | 5 |
| 005 | caucasian | 165 lb | 2 | 5 | 2 | 5 |
| 006 | caucasian | 191 lb | 2 | 5 | 1 | 5 |
| 007 | caucasian | 190 lb | 2 | 5 | 2 | 5 |
| 008 | caucasian | 142 lb | 2 | 5 | 2 | 5 |
| 009 | caucasian | 200 lb | 1 | 5 | 1 | 5 |
| 010 | caucasian | 180 lb | 2 | 5 | 2 | 5 |
| 011 | caucasian | 150 lb | 1 | 5 | 1 | 5 |

*Patient identifiers have been coded for HIPAA compliance

As shown in Table 2, all 11 patients were healed within 48-72 hours and symptoms completely resolved for all within 1 week. No patients experienced any adverse events. This study is ongoing and approximately 20 to 30 total patients will be recruited.

Other Embodiments

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A composition comprising:
sunflower seed oil present in an amount of about 25% to about 75% w/w of the composition;
olive oil present in an amount of about 1% to about 10% w/w of the composition;
lidocaine present in an amount of about 5% w/w of the composition;
zinc oxide present in an amount of about 25% w/w of the composition;
niacinamide present in an amount of about 5% w/w of the composition; and
beeswax present in an amount of about 1% to about 20% w/w of the composition.

2. The composition of claim 1 wherein the composition comprises:
sunflower seed oil present in an amount of about 50% w/w of the composition;
olive oil present in an amount of about 5% w/w of the composition;
lidocaine present in an amount of about 5% w/w of the composition;
zinc oxide present in an amount of about 25% w/w of the composition;
niacinamide present in an amount of about 5% w/w of the composition; and
beeswax present in an amount of about 10% w/w of the composition.

3. The composition of claim 1, wherein the composition further comprises colloidal oatmeal.

4. The composition of claim 1, wherein the composition further comprises a pharmaceutically acceptable butter and the pharmaceutically acceptable butter is selected from the group consisting of: shea butter, cocoa butter, illipe butter, mango butter, almond butter, kokum butter, sal butter, cupuacu butter, aloe butter, avocado butter, chaulmoogra butter, dhupu butter, hemp butter, kukui nut butter, macademia nut butter, jojoba butter, tucuma butter, and a combination thereof.

5. The composition of claim 1, wherein the composition is in the form of a paste, gel, cream, spray, suppository, mousse, emollient, ointment, foam, or suspension.

6. A method for reducing itching in a subject in need thereof, the method comprising administering to the subject a therapeutically effective amount of a composition comprising:
sunflower seed oil present in an amount of about 25% to about 75% w/w of the composition;
olive oil present in an amount of about 1% to about 10% w/w of the composition;
lidocaine present in an amount of about 5% w/w of the composition;
zinc oxide present in an amount of about 25% w/w of the composition;

niacinamide present in an amount of about 5% w/w of the composition; and beeswax present in an amount of about 1% to about 20% w/w of the composition.

7. The method of claim 6, wherein the itching is pruritus ani.

8. The method of claim 7, wherein the pruritus ani is associated with one or more of the following: diarrhea, rectal incontinence, stool leakage, a parasitic infection of the GI tract, excess anal moisture, excess anal perspiration, fungal overgrowth in the anal region, psoriasis, Crohn's disease, a hemorrhoid, an anal fissure, a bacterial skin infection, a viral infection, seborrheic dermatitis, atopic dermatitis, contact dermatitis, lichen planus, lichen simplex, lichen sclerosis, diabetes mellitus, leukemia and lymphoma, kidney failure, a liver disease, iron deficiency anemia, and hyperthyroidism.

9. The method of claim 6, wherein at least a portion of the skin of the subject itches.

10. The method of claim 6, wherein the itching on the subject is located on the head, an arm, torso, a leg, neck, a hand, or a foot of the subject.

11. The method of claim 6, wherein the composition comprises:

sunflower seed oil present in an amount of about 50% w/w of the composition;

olive oil present in an amount of about 5% w/w of the composition;

lidocaine present in an amount of about 5% w/w of the composition;

zinc oxide present in an amount of about 25% w/w of the composition;

niacinamide present in an amount of about 5% w/w of the composition; and beeswax present in an amount of about 10% w/w of the composition.

12. The method of claim 6, wherein the composition further comprises colloidal oatmeal.

13. The method of claim 6, wherein the composition further comprises a pharmaceutically acceptable butter and the pharmaceutically acceptable butter is selected from the group consisting of: shea butter, cocoa butter, illipe butter, mango butter, almond butter, kokum butter, sal butter, cupuacu butter, aloe butter, avocado butter, chaulmoogra butter, dhupu butter, hemp butter, kukui nut butter, macademia nut butter, jojoba butter, tucuma butter, and a combination thereof.

14. The method of claim 6, wherein the composition is in the form of a paste, gel, cream, spray, suppository, mousse, emollient, ointment, foam, or suspension.

15. The method of claim 7, wherein the composition comprises:

sunflower seed oil present in an amount of about 50% w/w of the composition;

olive oil present in an amount of about 5% w/w of the composition;

lidocaine present in an amount of about 5% w/w of the composition;

zinc oxide present in an amount of about 25% w/w of the composition;

niacinamide present in an amount of about 5% w/w of the composition; and beeswax present in an amount of about 10% w/w of the composition.

16. The method of claim 7, wherein the composition further comprises colloidal oatmeal.

17. The method of claim 7, wherein the composition further comprises a pharmaceutically acceptable butter and the pharmaceutically acceptable butter is selected from the group consisting of: shea butter, cocoa butter, illipe butter, mango butter, almond butter, kokum butter, sal butter, cupuacu butter, aloe butter, avocado butter, chaulmoogra butter, dhupu butter, hemp butter, kukui nut butter, macademia nut butter, jojoba butter, tucuma butter, and a combination thereof.

18. The method of claim 7, wherein the composition is in the form of a paste, gel, cream, spray, suppository, mousse, emollient, ointment, foam, or suspension.

* * * * *